United States Patent [19]

Hou

[11] 4,404,285

[45] Sep. 13, 1983

[54] PROCESS FOR PREPARING A ZERO STANDARD SERUM

[75] Inventor: Kenneth C. Hou, San Antonio, Tex.

[73] Assignee: AMF Incorporated, White Plains, N.Y.

[21] Appl. No.: 276,982

[22] Filed: Jun. 24, 1981

[51] Int. Cl.³ .................. G01N 33/78; G01N 33/96; B01D 39/18; B01D 39/02; B01D 39/04; B01D 39/06

[52] U.S. Cl. .................. 436/16; 436/500; 436/17; 436/174; 436/177; 252/426; 252/427; 252/428; 435/7; 210/690; 210/691; 210/692; 210/693; 210/694; 210/502; 210/505; 210/508; 210/661; 210/670; 210/679

[58] Field of Search ................ 23/230 B, 230.6; 252/408; 424/1, 1.5, 12; 435/7; 210/692, 693, 661, 604, 670, 679, 690, 691, 502, 505, 508; 252/427, 426, 428; 436/500, 16, 17, 174, 177

[56] References Cited

U.S. PATENT DOCUMENTS

| | | | |
|---|---|---|---|
| 1,787,467 | 1/1931 | Bender et al. | 424/1 |
| 3,149,023 | 9/1964 | Bodendore et al. | 424/1 |
| 3,414,383 | 12/1968 | Murphy | 424/1 |
| 3,442,819 | 5/1969 | Herbert | 252/428 |
| 3,615,222 | 10/1971 | Mead | 23/230 B |
| 3,666,854 | 5/1972 | Eisentraut | 424/1 |
| 3,743,482 | 7/1973 | Eisentraut | 424/1 |
| 3,775,615 | 11/1973 | Eisentraut | 23/230.6 |
| 3,776,698 | 12/1973 | Eisentraut | 424/1 |
| 3,911,096 | 10/1975 | Chopra | 424/1 |
| 3,953,360 | 4/1976 | Morishita et al. | 252/428 |
| 3,972,818 | 8/1976 | Bokros | 210/505 |
| 4,076,892 | 2/1978 | Fennimore et al. | 424/1 |
| 4,115,534 | 9/1978 | Ithakissios | 424/1 |
| 4,115,537 | 9/1978 | Driscoll et al. | 23/230.6 |
| 4,139,604 | 2/1979 | Gutcho | 424/1.5 |
| 4,147,764 | 4/1979 | Levy et al. | 424/1 |
| 4,169,051 | 9/1979 | Satoh et al. | 252/428 |
| 4,197,287 | 4/1980 | Piasio et al. | 23/230.6 |
| 4,305,782 | 12/1981 | Ostreicher et al. | 210/503 |
| 4,309,247 | 1/1982 | Hou et al. | 424/1 |
| 4,321,288 | 3/1982 | Ostreicher | 424/1 |

*Primary Examiner*—Teddy S. Gron
*Attorney, Agent, or Firm*—Oblon, Fisher, Spivak, McClelland & Maier

[57] ABSTRACT

A method for the removal of hormones from whole human serum which comprises: contacting, at a pressure higher than 1 psi the serum with a composite sheet, the composite sheet comprising a matrix of self-bonding fibers having interdispersed therein carbon particles, such that better than 90% of the carbon particles have an average diameter less than about 50 microns; and recovering a whole human serum having substantially undetectable amounts of hormones. The method is particularly useful for the removal of thyroid hormones.

17 Claims, 4 Drawing Figures

PROCESS FOR PREPARING A ZERO STANDARD SERUM

BACKGROUND OF THE INVENTION

1. Field of the Invention

The present invention relates to a process for the preparation of zero standard sera useful in immunoassay techniques.

2. Description of the Prior Art

Radioligand hormone assays have now become routine in hospital laboratories throughout the world. The key to the sensitivity of the test is the availability of hormone-free sera to be used as negative controls and also as diluents.

For example, standard controlled serum which contains no thyroxine is necessary in order to obtain the zero point for the standard curve used in radioimmunoassays or immunoradiometric assays or enzyme immunoassays. In addition, the use of zero standard control serum is also necessary to obtain accurate readings of hyperthyroid serum. Thus, when zero standard control serum is available, hyperthyroid serum can be diluted by a known factor with the zero standard control serum. T4 tests are then run by the above-identified procedures and compared with values obtained from standard curves. After the readings are obtained from these curves, dilution factors are applied to the readings. Accurate factors are only obtained when the zero standards have very low levels of hormones.

Eisentraut, U.S. Pat. No. 3,776,698, for example, prepares zero standard serum by contacting a quantity of acidified serum with a particulate inorganic crystalline sorbent material which is selected from the group consisting of phosphates, oxides, hydroxides, silicates, carbonates, aluminates, and sulfates, of the metallic elements in groups IA, IIA, IIIA, IIB and VIII of the periodic table.

In addition, two alternative sources of hormone-free serum are also presently used: (1) serum made by accumulation of a pool of serum from patients with hypopituitarism who are on replacement thyroxine therapy, or (2) serum made by extended high speed centrifugation of free carbon-adsorbed serum from a healthy population.

The use of free carbon, however, carries with it difficulties in time and equipment, when large volumes of serum are to be processed.

In order to be able to remove thyroid hormones (such as T3 and T4) from the serum, it is necessary to provide certain effective pore sizes in the treating carbon. Commercially available carbon is usually made by activating the same with steam at temperatures around 1000° C. The activation probably removes tars and insertion materials trapped between the naturally layered structure of the carbon, thus allowing access to the interlayer regions. The gain in surface area which is obtained, however, results in sacrifice of the structural rigidity of the final product.

The mechanical forces imposed on mixing the carbon with serum at high speed centrifugation are sufficient to fragment the fragile activated carbon structure. The supernatant serum normally contains carbon fragments visible as the appearance of dark color. Removal of the tiny carbon fragments from the serum requires the addition of technical grade kaolin, which acts as a gathering agent, followed by further mixing and centrifugation. Sometimes, even colloidal flocculation is not satisfactory for complete removal, and filtration through a micron size membrane is required.

Large carbon granules (having a range of about 400 microns in diameter) show poor efficiency of thyroid hormone removal, whereas smaller powdered carbon granules, while more efficient, are far too slow in the absence of pressure.

An attempt to increase the rate of hormone removal, by artificially providing a pressure differential across a bed of carbon particles so as to increase the availability of the inside pores of small powdered carbon structure to the hormone molecules, runs into various problems. The structural rigidity of the carbon particles may be insufficient to withstand the applied pressure, and the pores may break with concomitant collapse of the particles. Also, channeling quickly occurs across the bed, followed by rapid loss in removal efficiency.

Carbon has been loaded on a sheet having particles homogeneously distributed and firmly retained therein, and having substantial freedom from ruboff, flaking and smudging, as described in Bodendorf et al, U.S. Pat. No. 3,149,023. The Bodendorf et al sheets, however, are used as cigarette filters, air filters, gas filters, wrappers for fruit and substances prone to discoloration or spoilage by gases in the atmosphere, deodorizer layers in laminated sheet products for sanitary napkins, and for surgical dressings for wounds, and the like. They are not used in the removal of thyroid hormones from serum.

The Bodendorf materials are not even described as being useful for high pressure applications and, most importantly, for high pressure applications in the treatment of a biological material such as serum, wherein the integrity and composition of the final product is critical.

In preparing zero standard serum, the final product should contain all the necessary natural serum components except the hormones. Inasmuch as possible, proteins, carbohydrates, lipids, vitamins, and salts should remain at substantially the same levels as prior to the treatment. There is no indication in Bodendorf et al that their carbon filled sheets can be used for the treatment of such delicate biological materials as human serum, that the treatments could be carried out at high pressures, and that they would result in selective removal of hormones.

In sum, a method for the removal of hormones from human serum to prepare zero standard serum which method is quick, inexpensive, and simple to operate, which uses materials which are simple to prepare, and which is nondestructive and non-modifying of the final standard product has not yet been described by the prior art.

A need therefore continues to exist for such a method, and the present invention fulfills that need.

SUMMARY OF THE INVENTION

It is therefore an object of the invention to provide a method for the preparation of human zero standard serum.

It is another object of the invention to provide a method for the selective removal of hormones, such as thyroid hormones, from human serum.

It is yet another object of the invention to provide a method for the removal of hormones from human serum by carbon treatment.

Still another object of the invention is to provide a human serum having substantially undetectable levels of hormones.

These and other objects of the invention as will hereinafter become more readily apparent, have been attained by providing:

A method for the removal of hormones from human serum, which comprises:

contacting, at a pressure of greater than 1 psi, said serum with a composite sheet, said composite sheet comprising a matrix of self-bonding fibers having interdispersed therein carbon particles, such that better than 90% of said carbon particles have an average diameter of less than about 50 microns.

The objects of the invention have also been attained by providing a human serum having less than about 1 femtogram/dl of human thyroid hormones.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
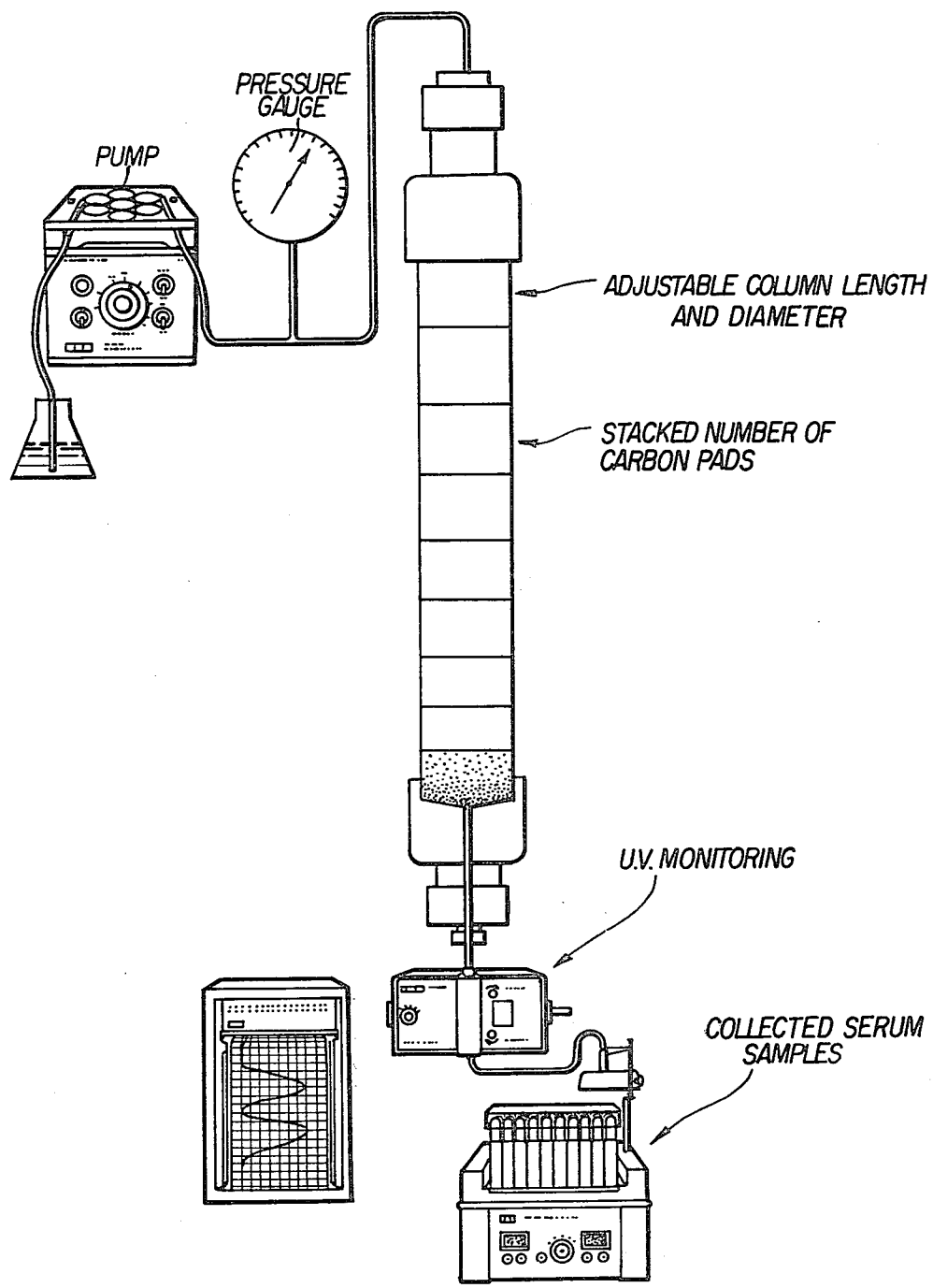
FIG. 1 is a schematic diagram of human serum treatment by sequentially stacked composite sheets in a cylindrical column.

The present inventor has discovered that a zero standard serum, having hormone levels comparable to the lowest heretofore available levels of hormones, such as thyroid hormones, can be rapidly and selectively prepared by contacting whole human serum with one or more composite sheets, each of said sheets comprising a matrix of self-bonding fibers having interdispersed therein highly refined carbon particles. The use of the composite sheet to remove the hormones is far superior to the use of carbon particles alone, either in slurry or packed in a bed.

By dispersing the carbon particles homogeneously in a matrix, it is possible to utilize pressure differentials during the contact of the serum with the particles, increasing the speed of the process without damaging the carbon structure.

Without being bound by any particular theory, Applicant speculates that the use of pressure differentials allow the hormones to interpenetrate the pores and interlayer spaces present in the three dimensional structure of activated carbon, and thus utilize the adsorption properties thereof to their fullest extent. The mechanical rigidity of the carbon particles is not harmed by the pressure differentials of the invention, since the particles are retained in the composite matrix structure. The serum samples obtained after contact contain no carbon fragments.

The use of pressure differentials also permits a substantial decrease in the time of processing.

Further, liquids to be treated with carbons packed in a bed have a general tendency to seek the passage with the least resistance, thus avoiding the most effective adsorptive surfaces. The present invention avoids the problem of commonly occurring channeling effects in packed particle columns due to the fixed position of carbon in the matrix.

The rate of adsorption in the column process is several orders of magnitude higher than that in powder mixing, since it eliminates the diffusion limiting factors, and replaces the same with kinetic mechanisms.

The use of matrix-bound carbon particles also has the advantage of providing the ability to recycle the serum therethrough as many times as necessary in order to utilize the available active sites in the carbon to their maximum capacity.

The carbon-containing composite sheets can be manufactured with different carbon loads and with different degrees of refinement of the fibers which form the self-bonding matrix. Variation of the load and fiber refinement allows for an accurate control of porosity of the composite sheet, a control which is not available when using free carbon particles. Controlling the porosity allows for the use of pressures within a wide range, the optimum to be chosen according to the particular commercial requirements and availability of instrumentation.

The term "hormones" as used in this invention is meant to include any steroid hormones and thyroid hormones present in human serum which can be adsorbed therefrom by the use of carbon. Examples of thyroid hormones are $T_3$ (tri-iodothyronine), $T_4$ (thyroxine), cortisol, or any other thyroid hormone which are assayed by an immunoassay system, or related assay system, and the levels of which need to be substantially undetectable in zero standard sera used in such assay systems. Examples of steroid hormones are the estrogens, androgens, corticoids and progestins.

The preparation of human serum from human blood is generally well known in the art and will not be described in great detail. Any process of preparing serum from human blood is useful to prepare the serum of the invention. For example, red blood cells are separated from the blood by centrifugation. The supernatant plasma is clotted as, for example, by addition of thrombin and calcium. Alternatively, blood is simply allowed to clot. The serum is separated by filtration or centrifugation from the clotted blood, and is ready for hormone removal.

The "whole" human serum used in this invention contains all the necessary physiological and biological ingredients such as proteins, hormones, enzymes, antibodies, vitamins, minerals, and the like, in the normal ranges of physiological concentration. Such serum is used as the starting serum in the process of the invention and, after said process, a serum is obtained which is essentially whole, except for the absence of hormones and, possibly, decreased levels of cholesterol.

The carbon-containing composite sheet comprises any type of fibers capable of being fibrated, e.g., polyethylene or cellulose fiber, and powdered carbon. The composite sheet may also contain other additives, as further described below.

The sheets can be prepared according to the process described by Hou and Ostreicher in U.S. Pat. No. 4,309,247.

In the discussion that follows, the preparation is described as related to cellulose fibers, but it is generally applicable to any kind of fibrilatable fiber.

Cellulose fibers, comprise preferably two discrete portions having species of markedly different dimensions. The major portion is composed of normal cellulose fiber; the minor portion is highly refined pulp.

The state of refinement of a wood pulp fiber is determined by means of a "freeness test" in which measurement of the flow rate through a forming pad of the fibers on a standard screen is determined. Two of the most common instruments for the measurement of freeness are the "Canadian Standard Freeness (CSF) Tester" and the "Schopper-Riegler Freeness Tester." In both of these methods, the quantity which is measured is the volume of water (expressed in ml) which overflows from a receiver containing an orifice outlet at the bottom. The (CSF) measurements are employed in the present specification.

Coarse unbeaten wood pulp fibers produce high drainage rates into the receiver from the screen resulting in a large overflow volume, and hence record a high freeness. Typical wood pulps show Canadian standard freeness values ranging from +400 ml to +800 ml. In paper or filter medium manufacture, such pulps may be subject to mechanical refining processes such as beating, which tends to cut and/or fibrilate the cellulose fibers. Such beaten fibers exhibit slower drainage rates and, therefore, lower freeness. The most highly refined pulps used in the paper industry are the so-called glassine pulps, which have been subjected to extended beating and exhibit Canadian standard freeness values of +80 to +100 ml.

If refining is continued beyond the glassine pulp condition, a point is reached where the measured freeness begins to increase with time. In this range of freeness, fiber fines are noted in the overflow stream, and it is evident that some of the solid matter is coming through the screen rather than forming a mat on it. As refining is continued, the quantity of fines in the overflow increases, as more and more of the material passes through the screen. The freeness in this range is described as "inverted" and, for convenience, is given a negative value (e.g. −200 ml). By use of special refining equipment and long refining time, it is possible to achieve inverted CFS values up to −1000 ml.

There are several types of pulp refiners commercially available and these fall into two basic categories, namely conical or Jordan types and disc types. The disc types, especially double disc refiners, appear to be particularly suitable for the preparation of the highly refined pulps of the invention.

The standard grade of wood pulp used in the invention (hereinafter "unrefined") has a Canadian standard freeness value of +400 to +800 ml. The unrefined pulp may comprise as little as 10% by wt. with up to 20–30% by wt. of the total weight of the sheet to provide filter media sheets with structural characteristics suitable for industrial serum treatment applications.

Highly refined pulp, having Canadian freeness values in the range +100 to −600 ml, is also added to the sheet of the invention, in a range of from 1–15% by total weight. In practice, there appears to be little advantage in using more than 10% by wt. of the highly refined pulp, or of using refined pulps exhibiting inverted Canadian freeness values greater than −600 ml. Generally, the weight ratio of unrefined to highly refined pulp will range from about 2:1 to 10:1, preferably 3:1 to 5:1.

If more than 30% wt of unrefined pulp is used, it is found that carbon particles leach out of the sheet during process. If more than 15% of highly refined pulp is used, the sheet becomes too tightly packed and flow-through efficiency decreases.

One composition, for example, would comprise 18–20% cellulose unrefined fiber, and 8–10% refined pulp, by weight of the total amount of the composite sheet.

Among the best compositions are those which contain 5% fiber having −250 CSF, 5% fiber having 0 CSF, 5% fiber having 40 CSF, and 15% fiber being unrefined.

The average diameter of the unrefined cellulose fiber is 30 to 50 microns while the average diameter of the highly refined pulp is normally less than about 1 micron.

Natural cellulose fibers such as manila hemp, jute, caroa, sissal, bleached or unbleached kraft, or kozu can be used in the present invention. Such natural cellulose fibers are preferred since no binder is necessary to provide strength to the sheet. A small amount of added binder material can nevertheless also be incorporated to enhance the bond formed by the cellulosic materials.

Binders such as malamine, polyamines, and polyamides in the order of 1% or less can be used. Reference is made to the following three patent applications which describe suitable resins and charge modifiers:

U.S. Ser. No. 074,376 filed Sept. 10, 1979 by Ostreicher, now U.S. Pat. No. 4,321,288, U.S. Ser. No. 147,975 filed May 8, 1980 by Ostreicher and Hou now U.S. Pat. No. 4,305,782, and U.S. Ser. No. 164,797, filed June 30, 1980 by Ostreicher and Hou. These applications are herein incorporated by reference.

The self-binding sheets may contain any type of carbon capable of adsorbing hormones from human serum, with the proviso that 90% or better of said carbon particles have an average diameter less than about 50 microns. This corresponds to highly refined carbon particles having greater than 270 mesh, most preferred greater than 325 mesh size. The use of larger carbon particle sizes decreases the efficiency or the process.

It is generally understood in the art that carbon structure is comprised of parallel layers of hexagonally ordered carbon atoms. When the carbon is not activated, the interlayer space is occupied by insert materials such as tars and other impurifying agents. Activation at high temperatures is necessary in order to purge the interlayer space. Activation is normally carried out at temperatures of 500°–2000° C. Examples of activated carbon materials useful in the present invention are Norit, LC-300 (sold by National Carbon Company), Darco and the like (sold by Atlas Powder Company). Most preferred among these is Norit.

The composite sheets of the invention may contain activated carbon in amounts of from about 10 to about 90% by wt. of carbon. Amounts lower than 10% are inefficient to provide sufficient removal capacity, while amounts greater than 90% cause problems such as undesirable removal of carbon from the sheets and into the final products. Preferably, the amount of carbon is 50–90%, most preferably 70–80%.

An additional advantage of using the matrix bound carbon particles in preparing zero standard sera according to the invention, is that the composite sheets can be prepared by incorporating thereinto hormone adsorbing amounts of other adsorbents such as ion exchange resins, or water soluble polymers which can further enhance the efficiency of the process by synergistic effects. Adsorbents used for thyroid hormone uptake in the prior art, and which may also be beneficially incorporated into the sheets of the invention include ion exchange resins disclosed in U.S. Pat. No. 3,414,383; non-ionic resin gels of cross-linked dextrans described by Murphy and Pattee, Journal of Clinical Endocrinology, 24:187 (1964); particulate inorganic crystalline materials described in U.S. Pat. No. 3,666,854; microspherical albumin, described in Rolleri et al, Journal of Nuclear Medicine, 13:893 (1972), and the like. The aforementioned disclosures are herein incorporated by reference.

In fabricating the carbon-containing sheets, any standard sheet-forming methodology of the art can be used. For example, the refined and unrefined fibers are first dispersed in water to a consistency of about 1%. Carbon is then added to the fiber slurry, followed by addition of a water soluble resin if necessary. Sufficient dispersion time is allowed before vacuum felting the slurry into a sheet form. Since water always has the tendency of choosing the least resistant passageway, the vacuum felting process provides a self-adjusting mechanism for uniform distribution of particles and fibers in the sheet structure. The sheets are conveniently formed on a foraminous surface, normally a woven wire mesh which, in practice, may vary from 50 mesh to 200 mesh, with mesh openings ranging from 280 micrometers to 70 micrometers, respectively. Finer meshes are unsuitable because of clogging problems and/or structural inadequacy.

The size of the openings in the foraminous vacuum felting surface, and the pore size of the cellulose fiber matrix of the form sheet, are quite large in comparison to some or all of the dimensions of the fine fiber or particulate components required to produce the desired submicronic filter media sheet.

The wet sheet is dried in an oven at about 300°-350° F. for 20 mins.-2 hrs.

The carbon-containing composite sheets obtained by this process have high strength when in the dry or in the wet state, and can be handled as sheets of paper.

The phrase "contacting . . . serum with . . . the composite sheet" as used in the invention is meant to include any available means of causing such contact. For example, the sheet can be be cut into disks or pads of variable diameters, and a plurality of such disks or pads can be stacked into properly fit cylindrical columns. Preswelling with buffer solution forces the disks snuggly onto the column edges without leakage. The choice of the number of disks installed in the column depends on the concentration of the hormones to be removed, and the balance between the tolerable pressure differential across the column and the rate of flow for the serum to be processed. A typical experimental setup is shown in FIG. 1.

Under standard operating conditions, a chromatographic column having a packing of stacked swollen disks or pads of composite sheets is provided with pressure resistant caps on both ends, and whole human serum is flowed through the column. One advantage of the present process is that the flow-through can be carried out at with pressure differentials using a standard peristaltic pump. Preferably, pressure differentials range between 1 and 200 psi, more preferably 1-50 psi, most preferably 1-20 psi. If the pressure falls below 1 psi, full utilization of the activated carbon pores is not effected and the process is too slow. Pressures higher than 200 psi can, of course, be used, especially in high performance liquid chromatographic systems, as long as instrumentation problems and pressure conrol problems do not render such processes expensive and cumbersome. A normal laboratory peristaltic pump working in the range of 1-20 psi can however be used with excellent results.

It is oberved that $T_3$ can optimally be removed at pressures higher than 5 psi; that $T_4$ can optimally be removed at pressures higher than 5 psi; and that cortisol can optimally be removed at pressures higher than 10 psi.

The number of sheet disks or pads in the column, the flow rate, the pressure differential across the filters, the use and number of serum recycles across the column, the carbon load, the fiber refinement, the temperature and the possibility of using regenerated sheets, are all variables which can be adjusted in the process.

When the pressure, carbon load and degree of refinement are all maintained within the previously discussed ranges, the remaining parameters are not critical and can be readily adjusted by those of ordinary skill in the art without further undue experimentation.

It is recommended that the temperature range from between 0° C. to 25° C., that the flow rate be between 0.1 and 5 ml/min, most preferably 0.2-2 ml/min, and that, for highest removal of thyroid hormones, the serum be cycled through the column more than once.

Optimization of all parameters can be carried out on a case-by-case basis, depending on the contigencies and need of the particular samples being cycled, as well as the available instruments. Optimization under a particular set of circumstances is further exemplified in the Examples shown below.

The serum obtained by the process of the invention is whole human serum, which contains substantially undetectable amounts of thyroid hormones. The term "substantially undetectable" as used in the present invention is meant to indicate that the presence of thyroid hormones in the serum is within normal background levels of the most accurate immuno assay systems available at the present time.

Thus, it is another embodiment of the invention to provide a whole human serum containing substantially undetectable levels of human thyroid hormones.

The levels of cortisol, $T_3$ and $T_4$ in the final product are less than 0.5 $\mu$g/dl, preferably less than 0.1 $\mu$g/dl.

The normal values or normal ranges of other components in whole human serum are subject to a wide components in whole human serum are subject to a wide variation, which depends on age, sex, and time, as well as the influence of hormones. Given this qualifying average, "normal" levels of various markers in human serum are provided herein as a means of further characterizing the final product of the invention: Vasopressin levels: 1-3 microunits/ml; albumin levels: 3.5-5 g/dl; globulin levels: 2-3.5 g/dl; and total cholesterol levels: 130-230 mg/dl.

The serum of the invention can be used as a standard in radioimmunoassay, enzyme immunoassay, agglutination immunoassay, and other such processes and systems. It can be supplied in assay kits or individually.

Having now generally described this invention, the same will become better understood by reference to certain specific examples, which are included herein for purposes of illustration only and are not intended to be limiting of the invention unless so specified.

I. General

A. Methods of Determining $T_3$, $T_4$ and Cortisol

The determination of $T_3$ and $T_4$, as well as cortisol, were performed using radio immunoassay kits commercially available. The kits are designed on the principle that radioactively labeled and unlabeled $T_3$ or $T_4$ or cortisol molecules compete for the binding sites on specific antibodies against $T_3$ or $T_4$. The amount of antibody used is such that its concentration in the final volume of incubate would bind approximately 50% of the labeled hormone in the absence of unlabeled hormone. As additional $T_3$ or $T_4$ or cortisol molecules are present in the controls or filtered samples, this amount of unlabeled $T_3$, $T_4$ or cortisol will compete with the labeled hormone molecules, and dilute the amount of radioactive molecules found in the bound state. A second antibody, goat anti-rabbit gammaglobulin, is added to help precipitate the complex of the first antibody bound to the hormone molecule. After centrifugation, the large antibody complex precipitates to the bottom of the test tube. The precipitates containing the bonded fraction can then be counted.

B. Fabrication of Carbon Filter Pads

The formulation of carbon pads according to the invention and used in the following Examples, are shown in Table 1.

TABLE 1

FORMULATION OF SHEET FABRICATION

| Filter No. | Cellulosic Coho | Microflake Component (−250) | Adsorbent | Treatment | Binder Resin | Felting Time | Filter Weight |
|---|---|---|---|---|---|---|---|
| 1-6-1 | 20% | 10% | 70% | no | no | 32 sec. | 15.1 g |
| 1-6-2 | 20% | 10% | 70% | no | polycup | 45 sec. | 15.4 g |
| 1-6-3 | 18% | 12% | 70% | 2.5% no | no polycup | 1.05 min | 15.3 g |

Carbon: Norit A from J. T. Baker in powder form
Cellulose: Wood pulp fiber
Microflake: Pulp beaten by mechanical force to be refined to small size [size?]
Binder Resin: Polycup 1884 is a polyamide resin manufactured by Hercules C. Chromatographic Column The column described in FIG. 1 was utilized. Carbon sheets were cut into disks of 25 mm, 47 mm, or 10 inch sizes and stacked into properly fit columns. Preswelling with buffer solutions forced the pads snugly into the column without leakage.

II. Examples

The adsorption of hormone from serum by mixing with carbon particles is a diffusion process. The rate of adsorption depends on the concentration difference between the unadsorbed hormone in serum, and the hormone absorbed on carbon. As more and more hormone is adsorbed in carbon, the concentration difference decreases, and this in turn reduces the rate of diffusion. In the adsorption by chromatographic column of the present invention, the rate is defined by a kinetic process, and the rate of adsorption can be controlled by the contacting time in the following manner:

contacting time = (Volume per Filter × Total Filters)/Flow Rate of Serum

The results obtained for a number of carbon filter colums are summarized in Table 2. The serum was cycled through the columns at a peristaltic pressure range of 2 to 50 psi.

TABLE 2

| Column Conditions | | Total No. of Cycles | Vol. of Serum Filtered | Components Measured | | | |
|---|---|---|---|---|---|---|---|
| Size of Filter | Total No. of Filters | | | Protein | $T_3$ | $T_4$ | Cortisol |
| 25 mm | 8 | original | | 72 mg/ml | 150 μg | 9 μg | 11 μg/dl |
| 25 mm | 8 | 6.6 | 100 ml | | | | 1.0 μg/dl |
| 25 mm | 8 | 7.0 | | 58 | 0 | 3.2 μg | 0.0 μg/dl |
| 25 mm | 77 | original | | 71 mg/ml | 135 μg | 8.75 μg | |
| | | 13.0 | 145 ml | 60 | <0 | 0.4 μg | |
| 25 mm | 13 at 10 ml/min. flow | original | | 63 mg/ml | 91.0 | 6.0 μg | |
| | | 1 | | 61 | 11.0 | 3.75 μg | |
| | | 12 | | 61 | <0 | 1.70 μg | |

The data demonstrates that regardless of the size of the filters, or the number of filters, the levels of thyroid hormone quickly decrease to levels close to zero, while the levels of proteins remain within the prior range.

III. Comparative Examples

In performing the Comparative Examples, the data is indicated in terms of counts per minute (cpm). Because of the nature of the radioimmunoassay method, the higher the cpm levels, the lower the level of hormones in the rsulting serum. Removal is calculated as follows by equation 1:

$$\% \text{ Removal} = \frac{\text{Specific Amount adsorbed}}{\text{Total amount to be adsorbed for acceptance}} = \frac{(\text{Sample Sera}) - (\text{Control Sera})}{(\text{Kit Zero}) - (\text{Control Sera})} \quad (1)$$

wherein (a) TC (total counts) = the total counts of the labeled $T_3$ or $T_4$ in the absence of any unlabeled $T_3$ or $T_4$ (i.e. the zero standard). Cpm levels are the highest in value;

(b) Control Sera = the unfiltered untreated human serum. Cpm levels are the lowest in this case, due to the highest concentration of unlabeled hormones;

(c) Sample Sera = sera filtered or adsorbed by carbon with cpm levels between total counts and control counts. The higher the cpm level readings, the more effective the removal or hormones from serum;

(d) Kit Zero=thyroid hormone free-human serum commercially available, and serving as standard. When cpm level readings in treated samples are higher than this value, it would mean that the unlabeled hormones in serum samples are even lower than the commercially available values, whereas when cpm level readings are lower, it means that only a small percentage of thyroid hormones has been removed.

From equation 1, 100% removal indicates that the amounts of thyroid hormones are removed down to the 100% acceptable level, as compared to the thyroid hormone free-human serum supplied with the commercial radioimmunoassay kits.

Comparison With Free Carbon Powders

Direct comparison of efficiency of hormone removal through adsorption by carbon in powder form versus carbon in composite sheet structures was conducted under the following side-by-side fixed conditions:

1. equal weight of carbon estimated based on the formulation of 70% carbon in the composite sheet;
2. equal ratio of adsorbate (serum) to adsorbent (carbon powder);
3. equal length of absorption time.

In all experiments, the weight amount of free carbon was mixed with 100 ml of serum by vortex shaking from time to time. Thus the serum was in contact with a bed of charcoal particles most of the time. The carbon powder was then removed from the serum by centrifugation. Minute particles left in the supernatant were removed by filtering through a 0.45 millimicron membrane before assay.

A. Effect on Adsorption Time

Figure 2:
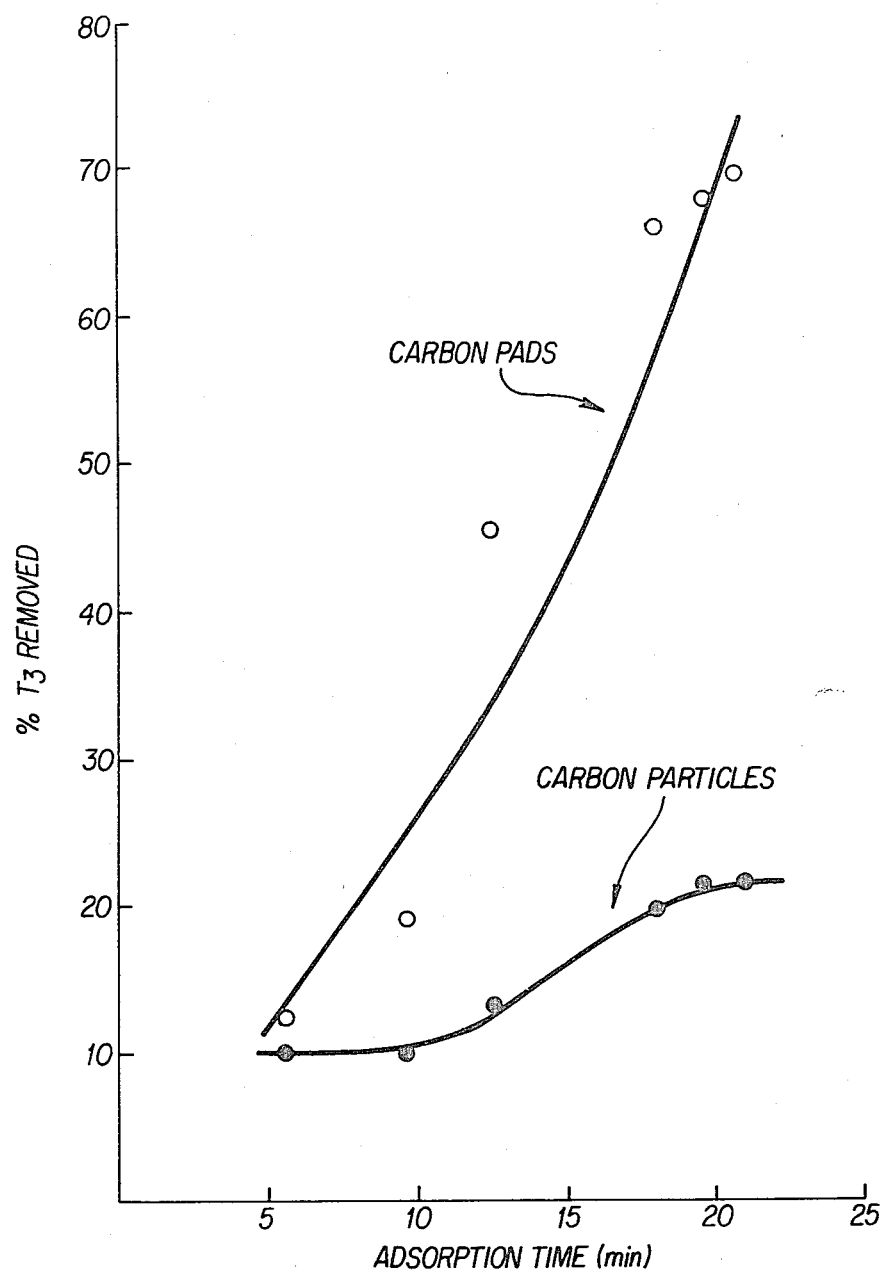
FIG. 2 shows the effect of adsorption time on the removal of $T_3$ from whole human serum using the composite carbon filled sheets of the invention, and using free carbon particles as comparison.

The linear effect on adsorption time for $T_3$ removal by carbon pads at serum pH can be seen in Table 3 and FIG. 2.

TABLE 3

Comparison of $T_3$ Removal from Human Serum by Carbon Particles vs. Carbon Pads
EFFECT ON ADSORPTION TIME

| Filter Type | No. of Filters | Adsorption Time (min) | Flow Rate (ml/min.) | ΔP Across The Filters (psi) | CPM (Counts/min.) | % Removal By Filter | CPM | % Removal By Particles |
|---|---|---|---|---|---|---|---|---|
| 1-6-1 | 5 | 6.5 | 1.54 | 5.5 | 3072 | 12.2% | 3058 | 11.3% |
| 1-6-1 | 5 | 9.0 | 1.10 | 6.2 | 3189 | 18.9% | 3037 | 10.2% |
| 1-6-1 | 5 | 12.5 | 0.95 | 6.8 | 3657 | 45.8% | 3101 | 13.8% |
| 1-6-1 | 10 | 18.0 | 0.55 | 6.2 | 4019 | 66.6% | 3208 | 20.0% |
| 1-6-1 | 10 | 19.3 | 0.52 | 5.5 | 4050 | 68.4% | 3281 | 24.0% |
| 1-6-1 | 10 | 21.3 | 0.47 | 6.8 | 4195 | 76.6% | 3287 | 24.5% |

Total Counts = 7832
Control Serum = 2860
Kit Zero = 4600

Since diffusion is a rather slow process, adsorption by carbon powder is expected to occur only on the external surface thereof, as shown in FIG. 2. The percentage of $T_3$ removal is doubled when doubling the amount of carbon used in the study.

B. Effect of Recycle of the Serum Through the Pads

Figure 3:
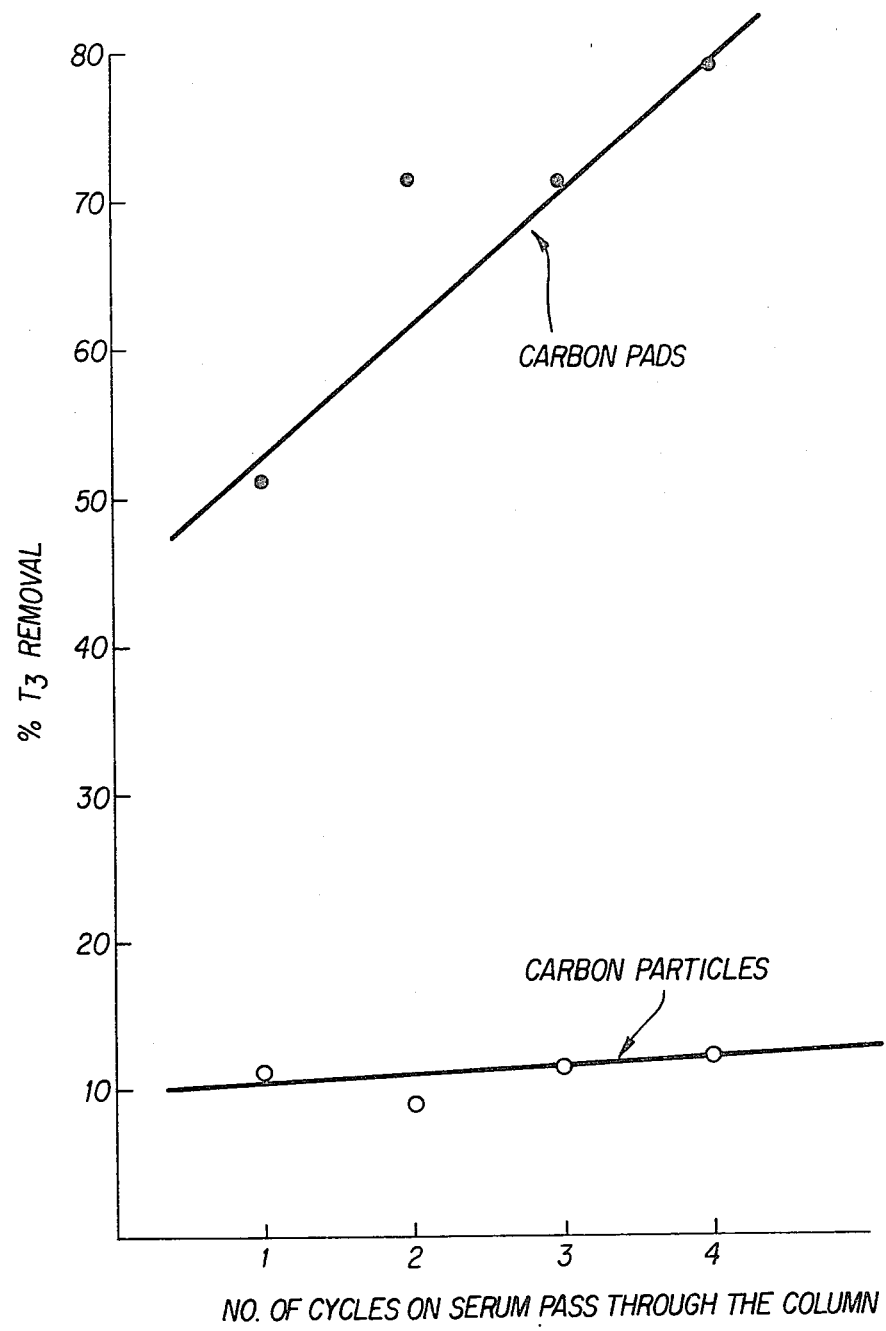
FIG. 3 shows the effect of recycling human serum on the removal of $T_3$ therefrom when using the carbon filled composite sheets of the invention, and when using free carbon particles as a comparison.

Table 4 and FIG. 3 exhibit the continuous removal of $T_3$ by recycling the serum through the pads, at serum pH.

TABLE 4

Comparison of $T_3$ Removal From Human Serum
By Carbon Particles vs. Carbon Pads
EFFECT ON SERUM RECYCLING THRU THE PADS

| Filter Type | No. of Filters | No. of Recycles | Flow Rate (ml/min.) | ΔP Across The Filters (psi) | CPM (Counts/min.) | % Removal By Filter | % Removal By Particles | CPM |
|---|---|---|---|---|---|---|---|---|
| 1-6-1 | 5 | 1 | 0.84 | 2.5 | 3891 | 51.2% | 10.5% | (3144) |
| " | " | 2 | " | 4.0 | 4273 | 72.0% | 8.4% | (3115) |
| " | " | 3 | " | 5.0 | 4261 | 71.4% | 11.7% | (3167) |
| " | " | 4 | " | 6.0 | 4407 | 79.3% | 11.8% | (3180) |

Total Counts = 7069
Control Serum = 2952
Kit Zero = 4786

The $T_3$ levels in serum are changed very little when free carbon particles are used.

C. Effect on the Number of Pads

The adsorption time can be controlled by either the flow rate or the number of pads installed in the column. Table 5 further demonstrates the advantage of controlling the flow rate and pad number in an adsorption study. These two major factors are not accessible in mixing with powdered carbon.

TABLE 5

Effect of Character and Number of Carbon Pads for $T_3$ Removal

| Filter Type | No. of Filters Applied | Flow Rate (ml/min.) | ΔP Across the Filters (psi) | CPM (Counts/min.) | % Removal By Filter | % Removal By Particle |
|---|---|---|---|---|---|---|
| 1-6-1 | 5 | 1.54 | 5.5 | 3072 | 12.2% | 11.4% |
| 1-6-1 | 10 | 0.52 | 5.5 | 4195 | 76.6% | 29.9% |
| 1-6-2 | 5 | 0.80 | 6.8 | 3257 | 24.1% | 13.8% |
| 1-6-2 | 10 | 0.47 | 6.8 | 3681 | 47.2% | 31.4% |

TABLE 5-continued

| | | Effect of Character and Number of Carbon Pads for $T_3$ Removal | | | | |
|---|---|---|---|---|---|---|
| Filter Type | No. of Filters Applied | Flow Rate (ml/min.) | ΔP Across the Filters (psi) | CPM (Counts/min.) | % Removal By Filter | % Removal By Particle |
| 1-6-3 | 5 | 1.10 | 6.5 | 3189 | 18.9% | 10.2% |
| 1-6-3 | 10 | 0.55 | 7.0 | 4019 | 66.6% | 32.5% |

Total Counts = 7833
Control Serum = 2838
Kit Zero = 4600

TABLE 6

| | | Effect of ΔP Across the Column of Carbon Pads For $T_3$ Removal | | | | | |
|---|---|---|---|---|---|---|---|
| Filter Type | No of Filters Applied | Flow Rate (ml/min.) | Δ P Across the Filters (psi) | CPM (Counts/min.) | % Removal By Filter | % Removal By Particles | |
| 1-6-1 | 5 | 1.54 | 5.5 | 3072 | 12.2% | 11.3% | (3058) |
| 1-6-1 | 5 | 0.91 | 21.0 | 3454 | 43.9% | 25.9% | (3172) |
| 1-6-2 | 5 | 0.80 | 6.8 | 3257 | 24.1% | 13.8% | |
| 1-6-2 | 5 | 0.80 | 28.0 | 3630 | 55.2% | | |

D. Effect of Δ P Across the Column

Figure 4:
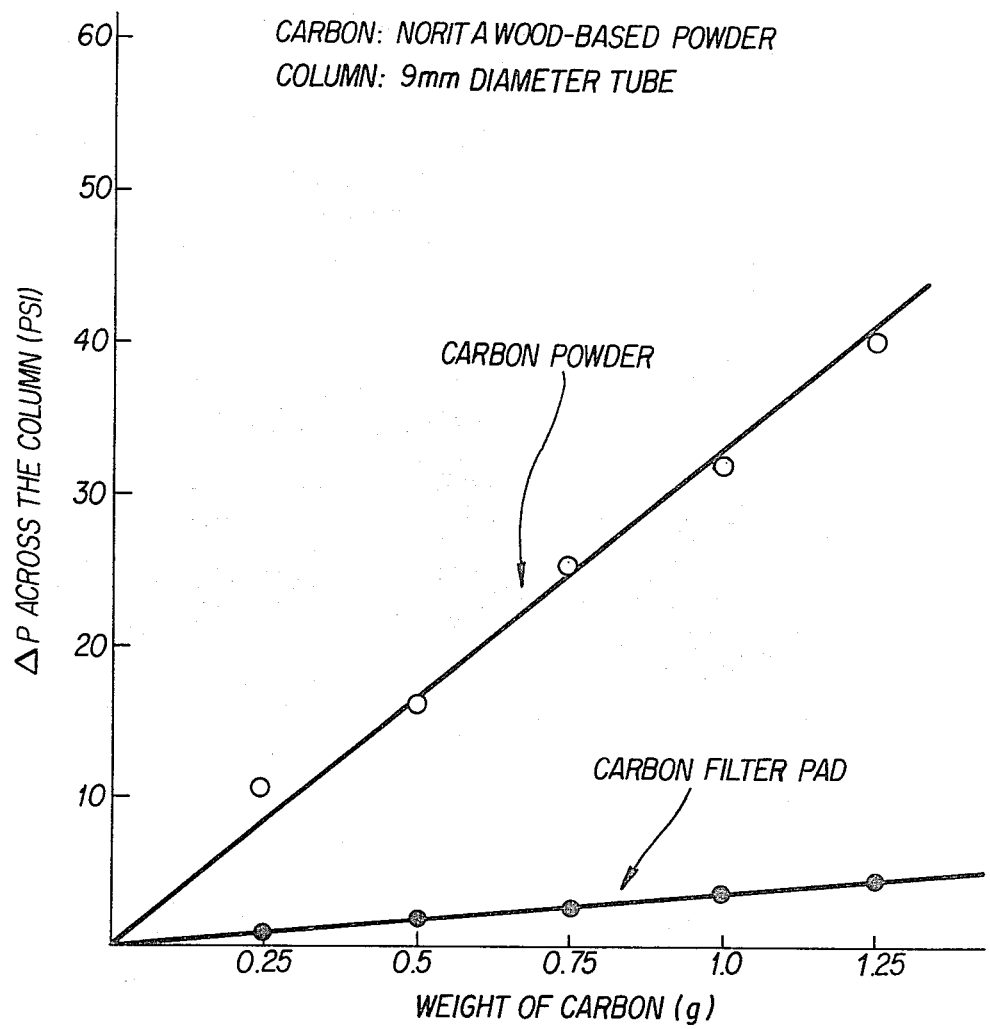
FIG. 4 shows the effect of pressure build-up when using a cylindrical column of 9 mm diameter packed with the carbon filled composite sheets of the invention, or packed with free carbon powder as a comparison.

Both the capacity and efficiency of hormone adsorption by carbon, rely on full utilization of its inner pores. It is speculated that the size of hormone molecules requires pressure build-up inside the column to force them to go into the pores in order to be adsorbed. It is a common phenomena that columns packed with carbon always form channels during filtration. The higher the pressure, the worse the occurrence of channel formation. The pressure build-up by packing carbon powders in a column is shown in FIG. 4. It is impractical and impossible to pack a column with powdered carbon for absorption at higher pressures. The technology of fabricating the carbon pads described in this invention provides a unique mechanism of fixing powdered carbon in specific positions to avoid channeling and adjusting the pad porosity for optimum pressure to accommodate the migration of molecules into the carbon inner pores. The effect of pressure differential for $T_3$ removal is shown in Table 6.

E. Effect of Regeneration of the Carbon Pads

The carbon activity fixed in pad form can be regenerated by eluting the hormones adsorbed thereon through pH or buffer adjustment, as shown in Table 7.

F. $T_4$ on Cortisol Removal

Studies on $T_4$ and cortisol removal are shown in Tables 8 and 9, at serum pH.

TABLE 7

| | | Effectiveness of Regenerating the Carbon Pads for $T_3$ Removal From the Human Serum | | | | | |
|---|---|---|---|---|---|---|---|
| Filter Type | No. of Filters | Vol. of Serum Filtered | Flow Rate (ml/min.) | ΔP Across The Filters (psi) | CPM (Counts/Min.) | % Removal By Filter | % Removal By Particles |
| (1) 1-6-1 | 3.0 | 100 ml | 1.80 | 11.0 | 2589 | 28.5% | |
| (2) 1-6-1 | " | 200 | 1.80 | 13.0 | 2536 | 24.7 | |
| (3) 1-6-1 | " | 300 | 1.80 | 15.0 | 2314 | 9.0 | |
| (4) 1-6-1 | " | 400 | 1.80 | 17.0 | 2226 | 3.0 | |
| (5) 1-6-1 | " | 500 | 1.80 | 20.0 | 2082 | 0.0 | |
| (6) 1-6-1 | " | 500 | 1.80 | | 2620 | 30.9 | |

(a) The pads installed in the column are saturated with $T_3$ as shown from the 0% of removal.
(b) Elution was performed by cycling 40 ml of 0.01 M PBS [what is PBS?] at pH 9.0 three times.
(c) After elution, the carbon pad regained its efficiency of $T_3$ removal as shown in the last entry #6.
Total Counts = 6333
Control Serum = 2185
Kit Zero = 3604

TABLE 8

| | | | Comparison of $T_4$ Removal From Human Serum by Carbon Particles vs. Carbon Pads | | | | | |
|---|---|---|---|---|---|---|---|---|
| Filter Type | No. of Filters | No. of Cycles | Flow Rate (ml/min.) | ΔP Across The Filters (psi) | CPM (Counts/min.) | By Filter | By Particles | (CPM) |
| 1-6-1 | 5 | 1 | 1.0 | 3.0 | 7831 | 61.7% | 4405 | 0.0% |
| " | " | 2 | " | 4.0 | 7965 | 64.5 | 4411 | 0.0% |
| " | " | 3 | " | 4.5 | 8188 | 69.2 | 4167 | 0.0% |
| " | " | 4 | " | 6.0 | 8644 | 78.8 | 4408 | 0.0% |

Total Counts = 17083
Control Serum = 4900
Kit Zero = 9650

TABLE 9
Comparison of Cortisol Removal from the Human Serum by Carbon Particles vs. Carbon Pads

| Filter Type | No. of Filters Applied | Flow Rate (ml/min.) | ΔP Across the Filters (PSI) | CPM (Counts/Min.) | % Removal By Filter | % Removal By Particles CPM | % Removal By Particles |
| --- | --- | --- | --- | --- | --- | --- | --- |
| 1-6-1 | 5 | 0.28 | 12 | 8950 | 67.6% | 7326 | 27.0% |
|  | 5 | 0.47 | 12 | 9381 | 81.9 | 7461 | 18.4 |
|  | 5 | 1.50 | 12 | 8837 | 63.9 | 7726 | 13.9 |
| Total Counts = 14,354 | | | | | | | |
| Control Serum = 6,906 | | | | | | | |
| Kit Zero = 9,929 | | | | | | | |
| 1-6-1 | 5 | 1.54 | 21 | 11,764 | 85.6% | 9528 | 21.0% |
| 1-6-2 | 5 | 0.80 | 29 | 11,386 | 74.7 | | |
| " | 10 | 0.67 | 41 | 11,457 | 76.7 | | |
| 1-6-3 | 5 | 0.77 | 34 | 10,967 | 62.6 | 10,062 | 36.4% |

Total Counts = 20,100
Control Serum = 8,803
Kit Zero = 12,262

It is speculated that $T_4$ being bulkier in size than $T_3$ requires somewhat longer diffusion times. The advantages of utilizing carbon pads are quite evident from the data.

Having now fully described this invention, it will be understood by those of ordinary skill in the art that the compositions, and parameters of manufacture and processing, as well as of the final products obtained therefrom, can be varied within a wide range of equivalents without affecting the spirit or scope of the invention or of any embodiments thereof.

What is claimed as new and intended to be covered by Letters Patent of the United States is:

1. A method for the removal of thyroid hormones from human serum which comprises:

flowing, at a pressure differential higher than 1 psi, said serum through a column containing a composite sheet, said composite sheet comprising a matrix of self-bonding fibers having interdispersed therein carbon particles, such that better than 90% of said carbon particles have an average diameter less than about 50 microns;

thereby removing said thyroid hormones from said serum.

2. The method of claim 1 wherein said thyroid hormones are selected from the group consisting of thyroxine, tri-iodo thyronine and cortisol.

3. The method of claim 1 wherein said pressure is 1-200 psi.

4. The method of claim 1 wherein said composite sheet comprises cellulose fiber and activated carbon.

5. The method of claim 4 wherein said cellulose fiber comprises 2-10: 1 by weight ratio of unrefined to highly refined pulp.

6. The method of claim 5 wherein said highly refined pulp has a Canadian Standard Freeness (CSF) value in the range +100 to −600 ml.

7. The method of claim 5 wherein said unrefined pulp has a Canadian Standard Freeness value in the range +400 to +800 ml.

8. The method of claim 5 wherein said unrefined pulp comprises 10-30% of the total weight of the sheet.

9. The method of claim 5 wherein said highly refined pulp comprises 1-15% of the total weight of the sheet.

10. The method of claim 5 wherein said unrefined pulp comprises 18-20% of the total weight of the sheet, and said highly refined pulp comprises 8-10% of the total weight of the sheet.

11. The method of claim 4 wherein said carbon is present in said sheet in hormone-adsorbing amounts.

12. The method of claim 11 wherein said amount is 10-90% of the total weight of said sheet.

13. The method of claim 4 wherein said sheet also comprises thyroid hormone adsorbing amounts of thyroid hormone adsorbing materials other than carbon.

14. The method of claim 1 wherein said composite sheet is present in the form of a plurality of essentially circular pads fitting the inside of a cylindrical column.

15. The method of claim 14 wherein the starting whole serum is allowed to flow through the column and sequentially contact each of said circular pads.

16. The method of claim 15 wherein said serum is recycled through said pad-containing column.

17. The method of any one of claims 1-13 wherein said removal is carried out at normal serum pH.

* * * * *